United States Patent
Rubinfeld (12)

(10) Patent No.: US 6,664,233 B1
(45) Date of Patent: *Dec. 16, 2003

(54) COMBINATION THERAPY INCLUDING 9-NITRO-20(S)-CAMPTOTHECIN AND BLEOMYCIN

(75) Inventor: Joseph Rubinfeld, Danville, CA (US)

(73) Assignee: SuperGen, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/709,967

(22) Filed: Nov. 10, 2000

Related U.S. Application Data

(63) Continuation of application No. 09/418,862, filed on Oct. 15, 1999, now Pat. No. 6,191,119.

(51) Int. Cl.$^7$ .................. A61K 31/70; A61K 31/44; A61K 38/00; A01N 43/04
(52) U.S. Cl. ................. 514/18; 514/23; 514/8; 514/34; 514/39; 514/283; 530/322
(58) Field of Search ................ 514/18, 34, 39, 514/283, 19, 8, 23; 530/322

(56) References Cited

U.S. PATENT DOCUMENTS

| | | | |
|---|---|---|---|
| 4,740,207 A | 4/1988 | Kreamer | 623/1 |
| 5,007,926 A | 4/1991 | Derbyshire | 623/1 |
| 5,053,007 A | 10/1991 | Euteneuer | 604/96 |
| 5,183,085 A | 2/1993 | Timmermans et al. | 140/89 |
| 5,342,307 A | 8/1994 | Euteneuer et al. | 604/103 |
| 5,352,236 A | 10/1994 | Jung et al. | 606/194 |
| 5,546,646 A | 8/1996 | Williams et al. | 29/407.08 |
| 5,604,233 A * | 2/1997 | Hausheer | 514/283 |
| 5,626,604 A | 5/1997 | Cottone, Jr. | 606/198 |
| 5,693,066 A | 12/1997 | Rupp et al. | 606/198 |
| 5,725,519 A | 3/1998 | Penner et al. | 606/1 |
| 5,786,344 A | 7/1998 | Ratain et al. | 514/100 |
| 5,800,517 A | 9/1998 | Anderson et al. | 623/1 |
| 5,810,873 A | 9/1998 | Morales | 606/198 |
| 5,836,952 A | 11/1998 | Davis et al. | 606/108 |
| 5,893,868 A | 4/1999 | Hanson et al. | 606/198 |
| 5,935,995 A * | 8/1999 | Bosslet | 514/460 |
| 5,964,730 A | 10/1999 | Williams et al. | 604/103 |
| 6,030,407 A | 2/2000 | Eidenschink | 606/198 |
| 6,123,720 A | 9/2000 | Anderson et al. | 623/1 |
| 6,132,450 A | 10/2000 | Hanson et al. | 606/198 |
| 6,152,944 A | 11/2000 | Holman et al. | 606/194 |
| 6,191,119 B1 * | 2/2001 | Rubinfeld | 514/34 |

FOREIGN PATENT DOCUMENTS

| | | |
|---|---|---|
| WO | WO97/20593 | 6/1997 |
| WO | WO98/19633 | 5/1998 |

OTHER PUBLICATIONS

Bernacki, Ralph J. et al., "In Vitro Antitumour Activity of 9–Nitro–Camptothecin as a Single Agent and in Combination with other Antitumor Drugs", Department of Pharmacology and Therapeutics, Roswell Park Cancer Institute, Buffalo, New York, AAN, N.Y. Acad. Sci., vol. 922, 2000, pp. 293–297.

Karaberis, E. and D. Mourelatos, "Enhanced Cytogenetic and Antitumor Effects by 9–Nitrocamptothecin and Antineoplastics", Laboratory of Biology and Genetics, Medical School, Aristotle University, Thessaloniki, Greece. Teratogenesis Carcinogenesis and Mutagenesis, vol. 20, No. 3, 2000, pp. 141–146.

Dainiak, Nicholas et al., "DNA Topoisomerase Inhibitors Block Erythropoiesis and Delay Hemoglobinization In Vitro", Journal of Cellular Physiology, vol. 138, No. 1, 1989, pp. 87–96.

Drewinko, B et al., "Combination Chemo Therapy In–Vitro with Adriamycin Observations of Additive Antagonistic and Synergistic Effects When Used in 2 Drug Combinations on Cultured Lymphoma Cells", Cancer Biochemistry Biophysics, vol. 1, No. 4, 1976, pp. 187–195.

Kaufmann, Scott H. "Antagonism between Camptothecin and Topoisomerase II–directed Chemotherapeutic Agents in a Human Leukemia Cell Line", Cancer Research, vol. 51, No. 4, 1991, pp. 1129–1136.

Guichard, Sylvie et al., "Cellular Interactions of 5–Fluorouracil and the Camptothecin Analogue CPT–11 (Irinotecan) in a Human Colorectal Carcinoma Cell Line" Biochemical Pharmacology, vol. 55, No. 5, Mar. 1, 1998, pp. 667–676.

Ciesielski, M.J. et al., "Synergistic cytotoxicity, apoptosis and protein–linked DNA breakage by etoposide and camptothecin in human U87 glioma cells: dependence on tyrosine phosphorylation" Journal of Neuro–Oncology, 1999, 41/3, pp. 223–234.

Giovanella, B.C. et al., "Enhanced antitumor effectiveness of camptothecin (CPT) and derivatives administered by continuous infusion through scheduling and combination with DNA damaging agents." Proceedings of the American Association for Cancer Research, vol. 36, Mar. 1991, p 391.

Database WPI, Section Ch, Week 199309, Derwent Publications Ltd., London, GB, Class B02, AN 1993–071029.

Takimoto, Chris H. and Susan G. Arbuck, "The Camptothecins", Cancer Chemotherapy and Biotherapy, 1996, Chabner, Philadelphia, pp. 463–484.

* cited by examiner

Primary Examiner—Christopher R. Tate
Assistant Examiner—Roy Teller
(74) Attorney, Agent, or Firm—Shirley Chen; Maya Skubatch; Wilson Sonsini Goodrich & Rosati

(57) ABSTRACT

A method for treating a patient having a disease associated with undesirable or uncontrolled cell proliferation such as cancer and restenosis is provided. The method comprises: delivering to the patient a therapeutically effective amount of 9-nitro-20(S)-camptothecin in combination with an effective amount of an antibiotic agent such as bleomycin.

4 Claims, No Drawings

COMBINATION THERAPY INCLUDING 9-NITRO-20(S)-CAMPTOTHECIN AND BLEOMYCIN

RELATED APPLICATIONS

This application is a continuation of U.S. patent application Ser. No. 09/418,862, filed Oct. 15, 1999, now U.S. Pat. No. 6,191,119 which is incorporated herein by reference in its entirety.

FIELD OF THE INVENTION

This invention relates to a method for treating disease using a camptothecin, and more specifically a method for treating disease using a camptothecin in combination with another drug.

DESCRIPTION OF RELATED ART

20(S)-camptothecin, a plant alkaloid, was found to have anticancer activity in the late 1950's. Wall, M. et al., *Plant antitumor agents. I. The isolation and structure of camptothecin, a novel alkaloidal leukemia and tumor inhibitor from Camptotheca acuminata*, J. Am. Chem. Soc. 88: 3888–3890, (1966); Monroe E. Wall et al., *Camptothecin: Discovery to Clinic*, 803 Annals of the New York Academy of Sciences 1 (1996). These documents, and all documents (articles, patents, etc.) cited to herein, are incorporated by reference into the specification as if reproduced fully below. The chemical formula of camptothecin was determined to be $C_{20}H_{16}N_2O_4$.

20(S)-camptothecin itself is insoluble in water. However, during the sixties and seventies the sodium salt of 20(S)-camptothecin was derived from 20(S)-camptothecin through opening of the lactone ring using a mild base. Clinical trials were then conducted using this hydrosoluble, sodium salt derivative of 20(S)-camptothecin (20(S)-camptothecin Na+), which was administered intravenously. The studies were later abandoned because of the high toxicity and low potency of 20(S)-camptothecin Na+. Gottlieb, J. A., et al., *Preliminary pharmacological and clinical evaluation of camotothecin sodium salt (NSC 100880)*, Cancer Chemother. Rep. 54:461–470(1979); Muggia, F. M., et al., *Phase I clinical trials of weekly and daily treatment with camptothecin (NSC 100880): Correlation with clinical studies*, Cancer Chemother. Rep. 56:515–521 (1972); Gottlieb, J. A. et al., *Treatment of malignant melanoma with camptothecin (NSC 100880)*, Cancer Chemother. Rep. 56:103–105 (1972); and Moertel, C. G., et al., *Phase II study of camptothecin (NSC 100880) in the treatment of advanced gastrointestinal cancer*, Cancer Chemother Rep. 56:95–101 (1972).

Despite its potential, interest in 20(S)-camptothecin as a therapeutic remained at a low ebb until the mid-1980's. By that time, drug therapies were being evaluated for treating human cancer using human cancer xenograft lines. During these evaluations, human tumors were serially heterotransplanted into immunodeficient, so-called "nude" mice, and the mice then tested for their responsiveness to a specific drug. (Giovanella, B. C., et al., *Cancer* 52(7): 1146 (1983)). The data obtained in these studies strongly support the validity of heterotransplanted human tumors into immunodeficient mammals, such as nude mice, as a predictive model for testing the effectiveness of anticancer agents.

20(S)-camptothecin, and later some of its substituted forms, elicited differential responses in the cell cycle of nontumorigenic and tumorigenic human cells in vitro. Although it is not yet understood why 20(S)-camptothecin and some of its substituted forms are cytostatic for nontumorigenic cells and cytotoxic for tumorigenic cells, the selective toxicity of the compounds against tumorigenic cells in vitro and in vivo was an especially interesting feature of these drugs.

Investigators began to experiment with various substituted forms of 20(S)-camptothecin. Good activity was found when various substitutions were made to the 20(S)-camptothecin scaffold. For example, 9-Amino-20(S)-Camptothecin (9AC) and 10,11-Methylendioxy-20(S)-Camptothecin (10.11 MD) are capable of having high anticancer activity against human colon cancer xenografts. Giovanella, B. C., et al., *Highly effective topoisomerase-1 targeted chemotherapy of human colon cancer in xenocrafts*, Science 246:1046–1048 (1989).

Additionally, 9-nitrocamptothecin (9 NC) has shown high activity against human tumor xenograft models. 9 NC has a nine position hydrogen substituted with a nitro moiety. 9 NC has inhibited the growth of human tumor xenografts in immunodeficient nude mice and has induced regression of human tumors established as xenografts in nude mice with little or no appearance of any measurable toxicity. D. Chatterjee et al., *Induction of Apoptosis in Malignant and Camotothecin-resistant Human Cells*, 803 Annals of the New York Academy of Sciences 143 (1996).

U.S. Pat. No. 5,552,154 to Giovanella et al. disclosed methods of treating specific forms of cancer with water-insoluble 20(S)-camptothecin and derivatives thereof, having the closed-lactone ring intact. In particular, transdermal, oral and intramuscular methods of administration using solutions of water-insoluble 20(S)-camptothecin were disclosed.

Other substituted 20(S)-camptothecin compounds that have shown promise include 7-ethyl-10-hydroxy 20(S)-camptothecin, and other 7, 9, 10, 11-substituted compounds.

A continuing need exists to develop new and improved ways to exploit the useful therapeutic activities of 20(S)-camptothecin and its various derivatives and analogs.

SUMMARY OF THE INVENTION

The present invention relates to new and improved compositions, kits, and methods for treating diseases using a combination therapy which includes 20(S)-camptothecin, an analog or 20(S)-camptothecin, or a derivative of 20(S)-camptothecin, collectively referred to herein as CPT. A therapeutic agent which exhibits a therapeutic synergistic effect with CPT is employed in the therapy.

A wide variety of non-CPT therapeutic agents with therapeutic synergistic effects with CPT may be employed. Examples of such nonCPT therapeutic agents include, but are not limited to alkylating agents, epidophyllotoxins, antimetabolites, antibiotics, and vinca alkaloids. Examples of alkylating agents include, but are not limited to cyclophosphamide, ifosfamide, melphalan, hexamethylmelamine, thiotepa and dacarbazine. Examples of antimetabolites include, but are not limited to 5-fluorouracil, cytarabine and folic acid analogs. Examples of folic acid analogs include, but are not limited to methotrexate, idatrexate or trimetrexate. Examples of antibiotics include, but are not limited to daunorubicine, doxorubicin, bleomycin or mitomycin. Examples of vinca alkaloids include, but are not limited to vinblastine, vincristine, and their synthetic analogues. Examples of epidophyllotoxin include, but are not limited to etoposide and teniposide.

The method may be used to treat a wide variety of diseases for which CPT has therapeutic activity. In one embodiment, the combination therapy methods and compositions of the present invention are useful in the treatment of neoplastic diseases.

DETAILED DESCRIPTION OF THE INVENTION

1. Camptothecin Compounds (CPT)

The class of camptothecin compounds referred to herein as CPT include various 20(S)-camptothecins, analogs of 20(S)-camptothecin. and derivatives of 20(S)-camptothecin. Camptothecin, when used in the context of this invention, includes the plant alkaloid 20(S)-camptothecin, both substituted and unsubstituted camptothecins, and analogs thereof. Examples of camptothecin derivatives include, but are not limited to, 9-nitro-20(S)-camptothecin, 9-amino-20(S)-camptothecin, 9-methyl-camptothecin, 9-chloro-camptothecin. 9-flouro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin. Prodrugs of camptothecin include, but are not limited to, esterified camptothecin derivatives as described in U.S. Pat. No. 5,731,316, such as camptothecin 20-O-propionate, camptothecin 20-O-butyrate, camptothecin 20-O-valerate, camptothecin 20-O-heptanoate, camptothecin 20-O-nonanoate, camptothecin 20-O-crotonate, camptothecin 20-O-2',3'-epoxy-butyrate, nitrocamptothecin 20-O-acetate, nitrocamptothecin 20-O-propionate, and nitrocamptothecin 20-O-butyrate.

In particular, when substituted camptothecins are used, a large range of substitutions may be made to the camptothecin scaffold, while still retaining activity. In a preferable embodiment, the camptothecin scaffold is substituted at the 7, 9, 10, 1 1, and/or 12 positions. Such preferable substitutions may serve to provide differential activities over the unsubstituted camptothecin compound. Especially preferable are 9-nitrocamptothecin, 9-aminocamptothecin, 10,11-methylendioxy-20(S)-camptothecin, topotecan, irinotecan, 7-ethyl-10-hydroxy camptothecin, or another substituted camptothecin that is substituted at least one of the 7, 9, 10, 11, or 12 positions.

Native, unsubstituted, camptothecin can be obtained by purification of the natural extract, or may be obtained from the Stehlin Foundation for Cancer Research (Houston, Tex.). Substituted camptothecins can be obtained using methods known in the literature, or can be obtained from commercial suppliers. For example, 9 nitrocamptothecin may be obtained from SuperGen, Inc. (San Ramon, Calif.), and 9-aminocamptothecin may be obtained from Idec Pharmaceuticals (San Diego, Calif.). Camptothecin and various of its analogs may also be obtained from standard fine chemical supply houses, such as Sigma Chemicals.

Particular examples of 20(S)-camptothecins include 9 nitrocamptothecin, 9-aminocamptothecin, 10,11-methylendioxy-20(S)-camptothecin, topotecan, irinotecan, 7-ethyl-10-hydroxy camptothecin, or another substituted camptothecin that is substituted at least one of the 7, 9, 10, 11, or 12 positions. These camptothecins may optionally be substituted.

2. Non-CPT Therapeutic Agents

A wide variety non-CPT therapeutic agents may have a therapeutic synergistic effect with CPT. Examples of such non-CPT therapeutic agents include but are not limited to alkylating agents, epidophyllotoxins, antimetabolites, and vinca alkaloids. Examples of alkylating agents include, but are not limited to cyclophosphamide, diethylnitroamine, ifosfamide, melphalan, hexamethylmelamine. thiotepa and dacarbazine. Examples of antimetabolites include, but are not limited to 5-fluorouracil, cytarabine and folic acid analogs. Examples of folic acid analogs include, but are not limited to methotrexate, idatrexate or trimetrexate. Examples of antibiotics include, but are not limited to daunorubicine, doxorubicin, bleomycin or mitomycin. Examples of vinca alkaloids include, but are not limited to vinblastine, vincristine, and their synthetic analogues. Examples of epidophylloxin include, but are not limited to etoposide and teniposide.

3. Indications for Combination Therapy

Preferable indications that may be treated using the combination therapies of the present invention include those involving undesirable or uncontrolled cell proliferation. Such indications include restenosis, benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Specific types of restenotic lesions that can be treated using the present invention include coronary, carotid, and cerebral lesions. Specific types of benign tumors that can be treated using the present invention include hemangiomas, acoustic neuromas, neurofibroma, trachomas and pyogenic granulomas. Specific types of cancers that can be treated using this invention include acute myelogenous leukemia, bladder, breast, cervical, cholangiocarcinoma, chronic myelogenous leukemia, colorectal, gastric sarcoma, glioma, leukemia, lung, lymphoma, melanoma, multiple myeloma, osteosarcoma, ovarian, pancreatic, prostrate, stomach, or tumors at localized sites including inoperable tumors or in tumors where localized treatment of tumors would be beneficial, and solid tumors. In a more preferable embodiment, the types of cancer include pancreatic, and/or colorectal. Treatment of cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

Abnormal angiogenesis that may be may be treated using this invention include those abnormal angiogenesis accompanying rheumatoid arthritis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

4. Compositions, Formulations, and Kits

Compositions according to the present invention might include a CPT, a non-CPT therapeutic agent, together with a pharmaceutical excipient. The composition preferably have a therapeutic synergy in the treatment of a disease, or a synergistic effect on the subjected being treated. As used herein, a synergistic effect is achieved when a greater therapeutic effect results with a combination therapy than using either drug or monotherapy alone. One advantage of combination therapy with a synergistic effect is that lower dosages of one or both of the drugs or therapies may be used so that the therapeutic index is increased and toxic side effects are reduced.

In an aspect, the invention is directed to kits comprising a container that contains the compound. In another aspect, the invention is directed to the kits, wherein the camptothecin is 9-nitrocamptothecin, or 9-aminocamptothecin. In still another aspect, the invention is directed to the kits, wherein the lactone ring protecting moiety is a polyalkylene oxide, dextran, polyvinyl alcohol, carbohydrate polymer, an antibody, streptozoticin or derivatives or mixtures thereof.

In still another aspect, the invention is directed to the kits, wherein the polyalkylene oxide is a polyethylene glycol.

In still another aspect, the invention is directed to kits comprising a container that contains the composition. In still another aspect, the invention is directed to the kits, wherein the camptothecin is 9-nitrocamptothecin, or 9-aminocamptothecin. In another aspect, the invention is directed to the kits, wherein the lactone ring protecting moiety is a polyalkylene oxide, dextran, polyvinyl alcohol, carbohydrate polymer, an antibody, streptozoticin or derivatives or mixtures thereof.

In still another aspect, the invention is directed to the kits, wherein the polyalkylene oxide is a polyethylene glycol.

5. Delivery of Therapeutic Agents

A wide variety of delivery methods and formulations for different delivery methods are intended to be encompassed by the combination therapies of the present invention.

The inventive combination of therapeutic agents may be administered as compositions that comprise the inventive combination of therapeutic agents. Such compositions may include, in addition to the inventive combination of therapeutic agents, conventional pharmaceutical excipients, and other conventional, pharmaceutically inactive agents. Additionally, the compositions may include active agents in addition to the inventive combination of therapeutic agents. These additional active agents may include additional compounds according to the invention, or one or more other pharmaceutically active agents. In preferable embodiments, the inventive compositions will contain the active agents, including the inventive combination of therapeutic agents, in an amount effective to treat an indication of interest.

The inventive combination of therapeutic agents and/or compositions may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The inventive combination of therapeutic agents and compositions may be administered by a variety of routes, and may be administered or coadministered in any conventional dosage form. Coadministration in the context of this invention is defined to mean the administration of more than one therapeutic in the course of a coordinated treatment to achieve an improved clinical outcome. Such coadministration may also be coextensive, that is, occurring during overlapping periods of time.

One therapeutically interesting route of administration or coadministration is local delivery. Local delivery of inhibitory amounts of inventive combination of therapeutic agents and/or compositions can be by a variety of techniques and structures that administer the inventive combination of therapeutic agents and/or compositions at or near a desired site. Examples of local delivery techniques and structures are not intended to be limiting but rather as illustrative of the techniques and structures available. Examples include local delivery catheters, site specific carriers, implants, direct injection, or direct applications.

Local delivery by a catheter allows the administration of a inventive combination of therapeutic agents and/or compositions directly to the desired site. Examples of local delivery using a balloon catheter are described in EP 383 492 A2 and U.S. Pat. No. 4,636,195 to Wolinsky. Additional examples of local, catheter-based techniques and structures are disclosed in U.S. Pat. No. 5,049,132 to Shaffer et al. and U.S. Pat No. 5,286,254 to Shapland et al.

Generally, the catheter must be placed such that the inventive combination of therapeutic agents s and/or compositions can be delivered at or near the desired site. Dosages delivered through the catheter can vary, according to determinations made by one of skill, but often are in amounts effective to create a cytotoxic or cytostatic effect at the desired site. Preferably, these total amounts are less than the total amounts for systemic administration of the inventive combination of therapeutic agents and/or compositions, and are less than the maximum tolerated dose. The inventive combination of therapeutic agents s and/or compositions delivered through catheters preferably should be formulated to a viscosity that enables delivery through a small treatment catheter, and may be formulated with pharmaceutically acceptable additional ingredients (active and inactive).

Local delivery by an implant describes the placement of a matrix that contains the inventive combination of therapeutic agents s and/or compositions into the desired site. The implant may be deposited by surgery or other means. The implanted matrix releases the inventive combination of therapeutic agents s and/or compositions by diffusion, chemical reaction, solvent activators, or other equivalent mechanisms.

Examples are set forth in Lange, Science 249:1527–1533 (September, 1990). Often the implants may be in a form that releases the inventive combination of therapeutic agents s and/or compositions over time; these implants are termed time-release implants. The material of construction for the implants will vary according to the nature of the implant and the specific use to which it will be put. For example, biostable implants may have a rigid or semi-rigid support structure, with inventive combination of therapeutic agents and/or composition delivery taking place through a coating or a porous support structure. Other implants made be made of a liquid that stiffens after being implanted or may be made of a gel. The amounts of inventive combination of therapeutic agents and/or composition present in or on the implant may be in an amount effective to treat cell proliferation generally, or a specific proliferation indication, such as the indications discussed herein.

One example of local delivery of the inventive combination of therapeutic agents and/or composition by an implant is use of a biostable or bioabsorbable plug or patch or similar geometry that can deliver the inventive combination of therapeutic agents and/or composition once placed in or near the desired site. An example of such implants can be found in U.S. Pat. No. 5,429,634 to Narciso, Jr.

A particular application of use of an implant according to the invention is treatment of cell proliferation in tissue that is not highly vascularized, as discussed briefly above. An example of such tissue is bone tissue. The difficulty in treating uncontrolled proliferative cell growth in bone tissue may be exemplified by the difficulties in treating bone tumors. Such tumors are typically refractory to treatment, in part because bone tissue is not highly vascularized. An implant in or near the proliferative site may potentially have localized cytotoxic or cytostatic effects with regard to the proliferative site. Therefore, in one embodiment, the invention may be used to treat bone tumors.

Another example of local delivery by an implant is the use of a stent. Stents are designed to mechanically prevent the collapse and reocclusion of the coronary arteries. Incorporating an inventive combination of therapeutic agents and/or composition into the stent may deliver the agent directly to or near the proliferative site. Certain aspects of local delivery by such techniques and structures are described in Kohn. Pharmaceutical Technology (October, 1990). Stents may be coated with the inventive combination of therapeutic agents and/or composition to be delivered. Examples of such techniques and structures may be found in U.S. Pat. Nos. 5,464,650 to Berg et al., 5,545,208 to Wolff et al., 5,649,977 to Campbell, 5,679,400 to Tuch, EP 0 716 836 to Tartaglia et al. Alternatively, the inventive combination of therapeutic agents and/or composition loaded stent may be biorotable, i.e. designed to dissolve, thus releasing the inventive combination of therapeutic agents and/or composition in or near the desired site, as disclosed in U.S. Pat. No. 5,527,337 to Stack et al. The present invention can be used with a wide variety of stent configurations, including, but not limited to shape memory alloy stents, expandable stents, and stents formed in situ.

Amounts of the inventive combination of therapeutic agents and/or composition delivered by the stent can vary, according to determinations made by one of skill, but preferably are in amounts effective to create a cytotoxic or cytostatic effect at the desired site. Preferably, these total amounts are less than the total amounts for systemic administration of the inventive combination of therapeutic agents and/or composition, and are preferably less than the maximum tolerated dose. Appropriate release times can vary, but preferably should last from about 1 hour to about 6 months, most preferably from about 1 week to about 4 weeks. Formulations including the inventive combination of therapeutic agents and/or composition for delivery of the agent via the stent can vary, as determinable by one of skill, according to the particular situation, and as generally taught herein.

Another example is a delivery system in which a polymer that contains the inventive combination of therapeutic agents and/or composition is injected into the target cells in liquid form. The polymer then cures to form the implant in situ. One variation of this technique and structure is described in WO 90/03768 to Donn.

Another example is the delivery of the inventive combination of therapeutic agents and/or composition by polymeric endoluminal sealing. This technique and structure uses a catheter to apply a polymeric implant to the interior surface of the lumen. The inventive combination of therapeutic agents and/or composition incorporated into the biodegradable polymer implant is thereby released at the desired site. One example of this technique and structure is described in WO 90/01969 to Schindler.

Another example of local delivery by an implant is by direct injection of vesicles or microparticulates into the desired site. These microparticulates may comprise substances such as proteins., lipids, carbohydrates or synthetic polymers. These microparticulates have the inventive combination of therapeutic agents and/or composition incorporated throughout the microparticle or over the microparticle as a coating. Examples of delivery systems incorporating microparticulates are described in Lange, Science, 249:1527–1533 (September. 1990) and Mathiowitz, et al., J. App. Poly Sci. 26:809 (1981).

Local delivery by site specific carriers describes attaching the inventive combination of therapeutic agents and/or composition to a carrier which will direct the drug to the desired site. Examples of this delivery technique and structure include the use of carriers such as a protein ligand or a monoclonal antibody. Certain aspects of these techniques and structures are described in Lange, Science 249:1527–1533.

Local delivery also includes the use of topical applications. An example of a local delivery by topical application is applying the inventive combination of therapeutic agents and/or composition directly to an arterial bypass graft during a surgical procedure. Other equivalent examples will no doubt occur to one of skill in the art.

The inventive combination of therapeutic agents s and/or compositions may be used in the form of kits. The arrangement and construction of such kits is conventionally known to one of skill in the art. Such kits may include containers for containing the inventive combination of therapeutic agents s and/or compositions, and/or other apparatus for administering the inventive combination of therapeutic agents and/or compositions.

It will be apparent to those skilled in the art that various modifications and variations can be made in the compounds. compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method for treating a patient having a disease associated with undesirable or uncontrolled cell proliferation sensitive to the combination below, comprising:

delivering to the patient a therapeutically effective amount of 9-nitro-20(S)-camptothecin in combination with a therapeutically effective amount of bleomycin, such that the efficacy of the therapy is enhanced through synergistic effects of 9-nitro-camptothecin and bleomycin.

2. The method according to claim 1, wherein the disease associated with undesirable or uncontrolled cell proliferation is cancer.

3. The method according to claim 2, wherein the cancer is selected from the group consisting of acute myelogenous leukemia, cholangiocarcinoma, chronic myelogenous leukemia, lymphoma, melanoma, multiple myeloma, osteosarcoma, gastric sarcoma, glioma, bladder, breast, cervical, colorectal, lung, ovarian, pancreatic, prostate, and stomach cancer.

4. The method according to claim 1, wherein the disease associated with undesirable or uncontrolled cell proliferation is restenosis.

\* \* \* \* \*